United States Patent [19]

Mathes

[11] 4,249,528
[45] Feb. 10, 1981

[54] MANUAL RESPIRATOR APPARATUS FOR USE WITH AUTOMATIC RESPIRATORS

[75] Inventor: Heinz Mathes, Lübeck, Fed. Rep. of Germany

[73] Assignee: Drägerwerk Aktiengesellschaft, Fed. Rep. of Germany

[21] Appl. No.: 6,195

[22] Filed: Jan. 24, 1979

[30] Foreign Application Priority Data

Feb. 17, 1978 [DE] Fed. Rep. of Germany ....... 2806750

[51] Int. Cl.³ .............................................. A61M 16/00
[52] U.S. Cl. ........................... 128/205.13; 128/205.24; 128/910
[58] Field of Search ............... 128/145.8, 145.6, 145.7, 128/145.5, 188, 142.2, 205.13, 204.28, 205.17, 910, 204.26, 205.24, 205.25

[56] References Cited

U.S. PATENT DOCUMENTS

| | | | |
|---|---|---|---|
| 3,043,302 | 7/1962 | Spears et al. | 137/505.42 X |
| 3,721,239 | 3/1973 | Myers | 137/312 X |
| 3,895,626 | 7/1975 | Elfstrand | 128/145.8 |
| 3,901,230 | 8/1975 | Henkin | 128/145.7 X |
| 3,967,619 | 7/1976 | Story et al. | 128/188 X |
| 3,993,059 | 11/1976 | Sjostrand | 128/145.7 X |
| 4,067,328 | 1/1978 | Manley | 128/145.7 X |
| 4,112,940 | 9/1978 | Parkes | 128/188 |

FOREIGN PATENT DOCUMENTS 910065 11/1962 United Kingdom ................ 128/205.13
1446432 8/1976 United Kingdom ..................... 128/910

OTHER PUBLICATIONS

Foregger, Air Products, "Scaveng-OR Gas Evacuator Illustrations," Printed in USA, 06001975, form No. 4P.

*Primary Examiner*—Henry J. Recla

*Attorney, Agent, or Firm*—McGlew and Tuttle

[57] ABSTRACT

A manual respirator apparatus for connection to an inhalation line connected between an automatic respirator and a patient and usable with a breathing gas supply under pressure, comprises, a block housing having a breathing gas supply inlet connected to the breathing gas supply, an inhalation line connectable to the inhalation line and an inhalation line outlet connectable to the patient and an exhalation inlet connected from the patient to the block housing. The block housing has a pressure chamber therein and is connected to an elastic breathing gas bag. A connection housing in the passage between the inlet from the gas supply line to the pressure chamber has adjusting valve means in the pressure chamber responsive to the pressure therein and to the fluctuation of the elastic breathing gas bag to permit flow of respirator gas through the connecting passage. A delivery passage is defined between the pressure chamber and the inhalation line and it contains one or more outlet valves which are openable at predetermined pressures to pass the respective gas from the pressure chamber into the inhalation line. The exhalation line is connected into the block housing at the location of a diaphragm chamber which has a diaphragm closing the exhalation gas inlet during the inhalation cycle. The diaphragm is pressured by a gas supplied from the pressure chamber and when this pressure chamber pressure goes down, the exhalation line opens to accept gas into the block housing. The exhalation gas is then passed outwardly, for example, for use in measurement devices and perhaps circulated back to the block housing for delivery through an anaesthesia gas scavenging bag and then eventual discharge to atmosphere.

3 Claims, 1 Drawing Figure

U.S. Patent
Feb. 10, 1981
4,249,528
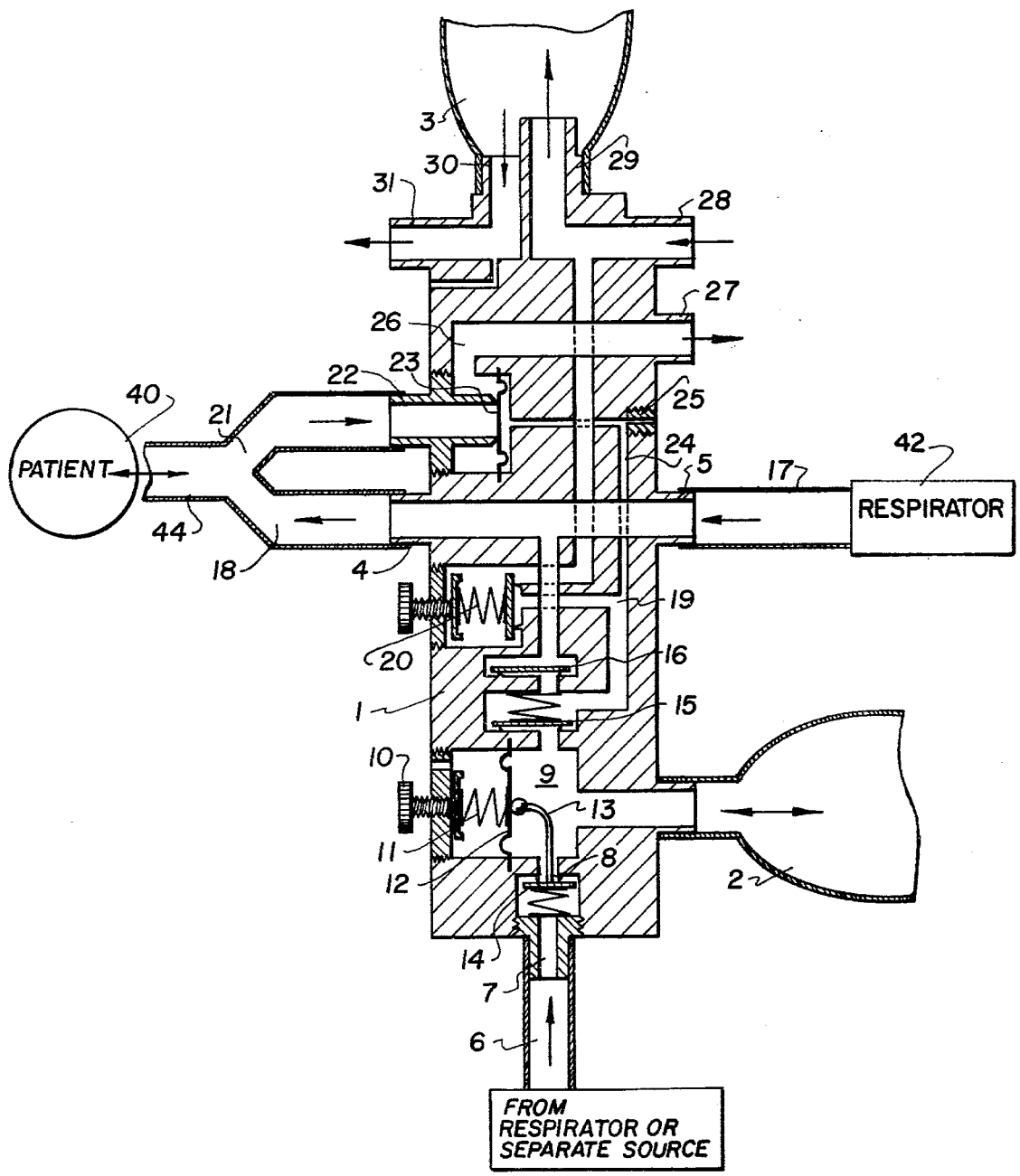

MANUAL RESPIRATOR APPARATUS FOR USE WITH AUTOMATIC RESPIRATORS

FIELD AND BACKGROUND OF THE INVENTION

This invention relates to respirators in general and, in particular, to a new and useful manual respirator apparatus for connection to an inhalation line connected between an automatic respirator and a patient, and which is usable with a breathing gas supply under pressure.

DESCRIPTION OF THE PRIOR ART

Respirators and/or anesthesia respirators are often controlled electronically and are thus dependent on an electirc power supply for their operation. In the event of a power failure, however, it is absolutely necessary for the patients to be continuously supplied with breathing gas. In this event, the breathing gas is supplied by a manual respirator apparatus. For the safe operation of such apparatus, it must be easy to connect as well as to operate.

A known respirator for manual operation has an elastically compressible reservoir bag. By rhythmic compression followed by its spontaneous expansion by means of the elastic recoil of this bag, oxygen-enriched gas is drawn from a container and forced into the patient's lungs through a line connected with the bag. For this purpose, the reservoir bag is equipped at its outlet end with an outlet valve connectable to a breathing mask or to an endotracheal tube, and, at its inlet end, it is provided with an inlet valve which is connected to an oxygen supply container. Upon compression of the reservoir bag, the outlet valve opens to expel of the breathing gas present in the bag while, at the same time, the inlet valve closes.

Upon expansion of the bag, the outlet valve is closed and the inlet valve opens, so that breathing gas can be sucked into the bag again. By means of a pressure equalizing vessel, which is also connected to the inlet valve, it is ensured that an overpressure which would cause the outlet valve to remain open cannot build up in the reservoir bag by the inflowing breathing gas. In that case, the patient would be pressurized by the breathing gas continuously and could not exhale. This known manually operated respirator cannot be connected to automatic respirators or to anesthesia respirators in order to take over the breathing gas supply in case of a power failure. (See German Offenlegungschrift DE-OS No. 24 24 798.)

A known respirator has a breathing gas reservoir arranged inside of a pressure chamber, with the interior of the reservoir being filled with breathing gas continuously through a check valve. By means of an electronic control, which operates at a given frequency and can be triggered additionally by spontaneous inhalation efforts of the patient, the pressure in the pressure chamber surrounding the breathing bladder is periodically increased through an injector operated by compressed air. The breathing gas reservoir is compressed here and its content is supplied to the patient via a shut-off valve which permits only this direction of flow.

At the same time, during inspiration, a pneumatically controlled exhalation valve arranged between the patient and a line for discharge of the exhaled gas is kept closed by the elevated pressure in the pressure chamber. If the breathing gas is to be supplied to the patient by hand, the pressure chamber surrounding the breathing gas reservoir is detached from a bayonet lock and removed. A switching valve operated by the pressure chamber switches the pneumatic control of the exhalation valve from the pressure chamber to the interior of the breathing gas reservoir. Otherwise, the path to the breathing gas remains the same. However, the breathing gas is then conveyed into the patient's lungs by manual compression of the breathing gas reservoir.

By the continuous supply of the breathing gas into the breathing gas reservoir, adaptation to fluctuations in the patient's needs is provided. If the supply is adjusted according to the highest need, gas losses will occur during other times due to outflow through the pressure limiting valve. Utilization of the existing breathing gas reservoir for supply of breathing gas by way of manual operation is possible only with respirators which contain a breathing gas reservoir or a breathing bag. (See German Offenlengungschrift DE-OS No. 26 18 949.)

SUMMARY OF THE INVENTION

The present invention provides a manual respirator apparatus for respirators and/or anesthesia respirators with which artificial respiration of the patient can be continued manually in case of a power failure.

In accordance with the invention, a manual respirator apparatus is connected into an inhalation line between the respirator and the patient and it has an inlet connectable to a breathing gas supply from a respirator under pressure. The apparatus includes a block housing having respective inlet and outlet lines connected into the inhalation line and to the patient and it also has an exhalation inlet line for receiving the exhaled gas from the patient. A pressure chamber defined in the housing is connected through a connecting passage to the inlet for the pressure gas through a delivery passage to the inhalation line. Adjustable valve means are provided in the pressure chamber which is connectable to an expansible and contractable elastic bag and it regulates the delivery of gas through the connecting passage from the breathing gas supply. Additional outlet valves are disposed in the delivery passage between the pressure chamber and the inhalation line for regulating the delivery of the breathing gas to the inhalation line in accordance with predetermined valve setting pressures.

The advantages achieved with the invention are, above all, the compact arrangement of the necessary elements, such as the valve block, with the breathing bag and the anaesthesia gas scavenging bag. Connection into the inhalation line is sufficient. Artificial ventilation then occurs in a simple and reliable manner directly through the elastic breathing bag. The breathing bag meters the quantity of breathing gas. Because of its elasticity, service personnel can feel the state of the patient's lungs and can then proceed accordingly in further artificial ventilation. The simple components can be made of materials which permit sterilization. Monitoring of the functional state presents no particular problems.

In a further design, the measuring devices of the automatic respirator to which the manual respirator apparatus is connected can be used in a simple manner for control of the respiration data, e.g., pressure, rate of flow and/or volume. The clinical personnel are protected by the anaesthesia gas scavenging bag and the connected excess gas scavenging apparatus from any anesthesia gases still contained in the exhaled gas which may escape.

Accordingly, an object of the present invention is to provide a manual respirator apparatus for connection to an inhalation line connected between a respirator and a patient and usable with a breathing gas supply from a respirator under pressure, which comprises, a block housing having a connection into the respirator line and to the patient and a pressure chamber defined therein with adjustable valve means for regulating the connection from the breathing gas supply into the pressure chamber, and wherein, the pressure chamber is connected to an elastic breathing gas bag and further including a delivery passage in the housing which connects from the pressure chamber to the inhalation line and has a plurality of separately set valves which are opened at predetermined pressures for supplying additional breathing gas to the inhalation line.

A further object of the invention is to provide a manual respirator apparatus for use with automatic respirators which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic sectional view of a manual respirator apparatus, constructed in accordance with the invention.

DESCRIPTION OF THE PREFERRED EMBODIMENT

Referring to the drawing in particular, the manual respirator apparatus in accordance with the invention, comprises, a valve block 1 with an elastic breathing gas bag 2 and a anaesthesia gas scavenging bag 3. It is inserted by the connections 4 and 5 into an inhalation line 17 between the patient 40 and the respirator 42.

The breathing gas from the respirator or from a separate supply 6 is fed into the inlet 7 in the valve block 1 under a pressure of up to 5 bar. The inlet valve 8 following inlet 7 is controlled by the pressure in chamber 9 or, respectively, by the pressure in the breathing gas bag 2. For this purpose, the desired pressure is adjusted by means of the compression spring 11 via an adjusting knob or setting knob 10. The pressure in chamber 9 acts on the valve disc 14 through the diaphragm or membrane 12 and rocker arm ("tilting lever") 13. At equilibrium between the pressure in chamber 9 and the compression spring 11, the rocker arm 13 is in an inoperative position, in which the inlet valve 8 is closed.

After the desired pressure has been reached, the breathing gas 2 is filled with the breathing gas. By compression, its content of respiratory gas is forced into the inhalation line 17 via the outlet valves 15 and 16. It then flows to the patient via the inhalation line or hose 18 which is connected at 4. Undue pressures in the inhalation tract are prevented by the adjustable overpressure valve 20 inserted via channel 19 behind the outlet valve 15.

Exhalation occurs via a mouthpiece 44 from the patient 40 to the exhalation line 21, connected in a known manner via a Y-piece. The exhalation line 21 is connected to the valve block 1 through the spout 22. During the inhalation phase, spout 22 is kept closed by the diaphragm or membrane 23 used as the exhalation valve. To this end, it is pressurized by the pressure of the breathing gas to be inhaled via channels 19 and 24.

Exhalation starts with the relief of the breathing bag 2. The outlet valves 15 and 16 close with decreasing pressure. Diaphragm 23 is thereby relieved, so that the exhaled gas can flow out. Any slight leakage at the outlet valves 15 and 16 does not present any obstacle. The small quantities of gas are vented into the atmosphere through the nozzle vent 25.

A spring biases valve 15 closed when the pressure in chamber 9 is equal to that in line 17. When the bag is compressed, pressure builds in chamber 9 to overcome the spring on valve 15. Valve 16 which is biased closed only by the pressure in line 17, now opens. The spring of valve 15 is strong enough to hold the pressure of chamber 9 when bag 2 is not compressed and valve 16 closes the inhalation line 17 to the channels 19, 24 and 25 at the same time.

For the determination of data, e.g., pressure, rate of flow and/or volume, the exhaled gas is supplied behind the diaphragm 23 through channel 26 and connection line 27 to the respective measuring devices of the respirator and is returned via connection 28. It then flows via connection line 29 into the anaesthesia gas scavenging bag 3, from which it is then removed by excess gas scavenging apparatus through the lines 30 and 31.

While a specific embodiment of the invention has been shown and described in detail to illustrate the application of the principles of the invention, it will be understood that the invention may be embodied otherwise without departing from such principles.

What is claimed is:

1. A manual respirator apparatus for connection to an inhalation line which is connectable between an automatic respirator and a patient and is also connected to means for supplying a breathing gas under pressure, comprising, a blocked housing having a breathing gas supply inlet connectable to the means for supplying a breathing gas under pressure, an inhalation line inlet in said housing connectable to the inhalation line, an inhalation line outlet in the housing connected to said inhalation line inlet and connectable to the patient, an exhalation line inlet connectable from the patient and connected to the housing for receiving the exhalation gas from the patient, said housing having a pressure chamber therein, an elastic breathing gas bag connected to said pressure chamber and being expandable and compressible during exhalation and inhalation to vary the pressure in said pressure chamber, a connection passage in said housing between said gas supply inlet and said pressure chamber, adjustable valve means in said pressure chamber and in said connection passage responsive to pressure in said pressure chamber and said breathing gas bag to permit flow of breathing gas through said connection passage to said breathing gas bag, a delivery passage between said pressure chamber and said inhalation line inlet, outlet valve means in said delivery passage openable at a predetermined pressure to pass breathing gas from said pressure chamber to said inhalation line inlet when said breathing gas bag is compressed, an exhalation line output in the housing connected to said exhalation line inlet for the venting of exhalation gas from the housing, a control chamber in said housing adjacent and connected to said exhalation line inlet, a diaphragm in said control chamber positioned to close said exhalation line inlet during inhalation and to open said exhalation line inlet during exhalation, and a pressure line connection between said control chamber with said diaphragm and said delivery passage for regulating the movement of said diaphragm in accordance with the pressure in said pressure chamber so that said exhalation line inlet is closed when said breathing gas bag is compressed, said outlet valve means comprising first and second outlet valve members arranged in series in said delivery passage and biasing means connected to said first and second valve outlet members for biasing said respective first and second outlet valve members toward closed positions thereof when said gas bag is not compressed to maintain the pressure in said pressure chambers and to close said inhalation line inlet with respect to said pressure line, said pressure line connection connected to said delivery passage between said first and second outlet valve members.

2. A manual respirator apparatus, as claimed in claim 1, including an overpressure chamber defined in said housing having a connection to said pressure chamber and overpressure valve means in said overpressure chamber for venting said overpressure chamber upon exceeding a predetermined pressure.

3. A manual respirator apparatus, as claimed in claim 1, including an anesthesia gas scavenging bag connected to said exhalation line output of said housing, and a first connection from said anesthesia gas scavenging bag to the exterior of said housing for receiving gases which have been analyzed.

* * * * *